(12) United States Patent
Broer et al.

(10) Patent No.: US 11,471,698 B2
(45) Date of Patent: Oct. 18, 2022

(54) TUNABLE LIGHT SOURCE

(71) Applicant: Lumitex, Inc., Strongsville, OH (US)

(72) Inventors: Peter Broer, Bratenahl, OH (US); Vedang Kothari, Cleveland, OH (US); Alan Greszler, Westlake, OH (US); Joe Dombrowski, Medina, OH (US); David Felty, Parma, OH (US); Mike Kerns, Stron, OH (US)

(73) Assignee: Lumitex, Inc., Strongsville, OH (US)

( * ) Notice: Subject to any disclaimer, the term of this patent is extended or adjusted under 35 U.S.C. 154(b) by 910 days.

(21) Appl. No.: 16/283,702

(22) Filed: Feb. 22, 2019

(65) Prior Publication Data

US 2019/0262629 A1 Aug. 29, 2019

Related U.S. Application Data

(60) Provisional application No. 62/634,386, filed on Feb. 23, 2018.

(51) Int. Cl.
| | |
|---|---|
| *A61N 5/06* | (2006.01) |
| *A61L 2/08* | (2006.01) |
| *A61L 2/10* | (2006.01) |
| *A61B 90/30* | (2016.01) |
| *A61B 90/98* | (2016.01) |

(52) U.S. Cl.
CPC ............ *A61N 5/0621* (2013.01); *A61B 90/30* (2016.02); *A61L 2/084* (2013.01); *A61L 2/085* (2013.01); *A61L 2/10* (2013.01); *A61N 5/0616* (2013.01); *A61B 90/98* (2016.02); *A61L 2202/11* (2013.01); *A61N 2005/0626* (2013.01); *A61N 2005/0659* (2013.01); *A61N 2005/0663* (2013.01)

(58) Field of Classification Search
CPC ............... A61N 5/0621; A61N 5/0616; A61N 2005/0626; A61N 2005/0659; A61N 2005/0663; A61B 90/30; A61B 90/98; A61L 2/084; A61L 2/085; A61L 2/10; A61L 2202/11
See application file for complete search history.

(56) References Cited

U.S. PATENT DOCUMENTS

| | | | |
|---|---|---|---|
| 8,569,715 B1 * | 10/2013 | Tantillo | A61L 2/10 250/455.11 |
| 2005/0017196 A1 * | 1/2005 | Fenc | A61L 2/10 250/455.11 |
| 2008/0269844 A1 * | 10/2008 | Logslett | A61N 5/0621 5/663 |

(Continued)

OTHER PUBLICATIONS

"ESCO Life Sciences, Ultraviolet Lamps & Interlock Kits, 2015, Lab Animal Research Products, https://escolifesciences.eu/lab-animal-research-products/accessories/ultraviolet-lamps-interlock-kits/4/7/" (Year: 2015).*

*Primary Examiner* — Joseph M Dietrich
*Assistant Examiner* — Michael T. Holtzclaw
(74) *Attorney, Agent, or Firm* — Grant J. Steyer

(57) ABSTRACT

An illuminated bassinet including a light source for delivering therapeutic light and anti-bacterial light, where an interlock prevents the anti-bacterial light from being emitted while an infant is located in the bassinet. Also, a surgical illuminator configured to concurrently or alternately emit different wavelengths of light for treating a physiological condition and for affecting perception of the surgical opening.

9 Claims, 4 Drawing Sheets

(56) References Cited

U.S. PATENT DOCUMENTS

| | | | |
|---|---|---|---|
| 2012/0215054 A1* | 8/2012 | Rodrigues | A61G 11/00 |
| | | | 600/22 |
| 2012/0223216 A1* | 9/2012 | Flaherty | G05D 1/0242 |
| | | | 901/1 |
| 2014/0031906 A1* | 1/2014 | Brezinski | A61N 5/06 |
| | | | 607/90 |
| 2015/0217132 A1* | 8/2015 | Makkapati | A61N 5/0621 |
| | | | 607/90 |
| 2018/0161593 A1* | 6/2018 | Palaniswamy | A61N 5/0621 |
| 2018/0185664 A1* | 7/2018 | Powell | A61N 5/0621 |

* cited by examiner

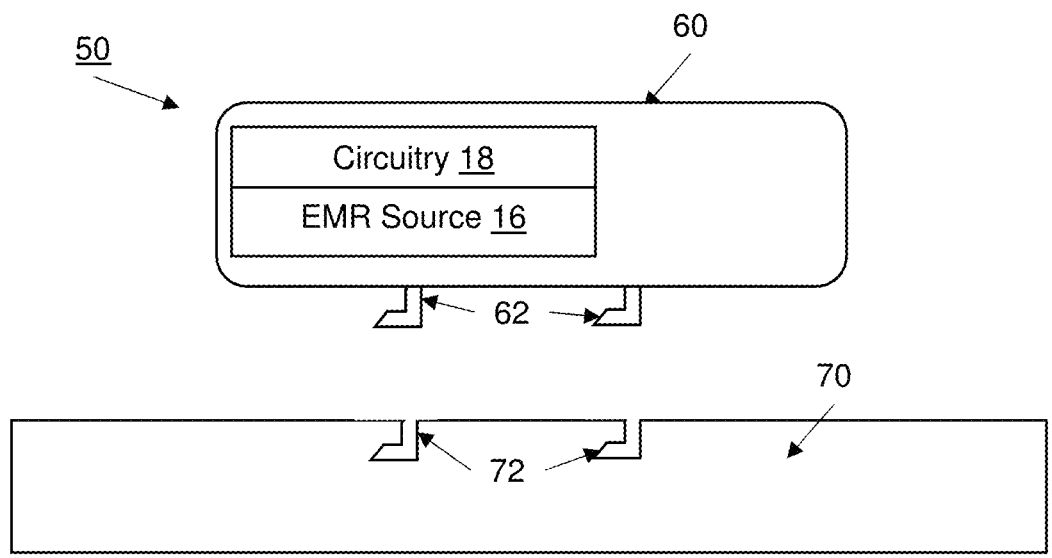
FIG. 9
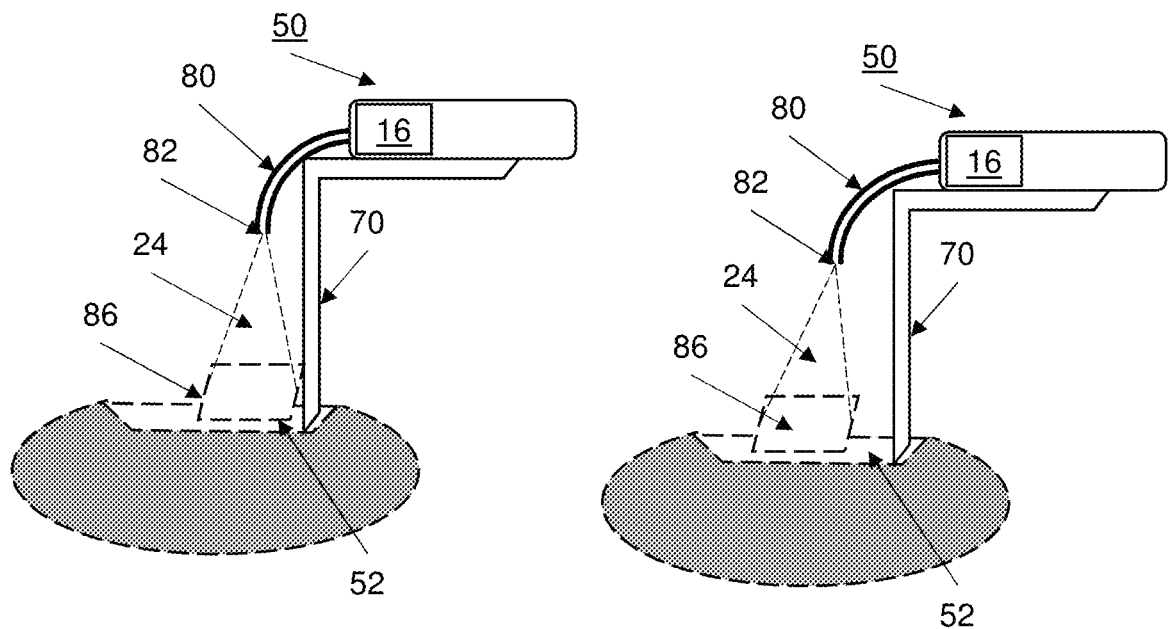
FIG. 10
FIG. 11

TUNABLE LIGHT SOURCE

RELATED APPLICATIONS

This application claims the benefit of Application No. 62/634,386 filed on Feb. 23, 2018, which is herein incorporated by reference in its entirety.

TECHNICAL FIELD

The present disclosure relates generally to light sources and, more particularly, to a tunable light source used in a hospital setting.

BACKGROUND

Approximately 60% of the infants born in the United States each year become clinically jaundiced. The most common therapy for treating jaundice in infants is phototherapy. Phototherapy facilitates the transformation of the compounds causing jaundice (i.e., unconjugated bilirubin) into compounds that are more easily excreted by the infant. Phototherapy is, however, not limited to treating jaundice, but may be used to treat many other issues.

For example, photobiomodulation (PBM) uses visible (400-700 nm) and near-infrared (700-1100 nm) light to elicit photophysical and photochemical events by involving endogenous chromophores. PBM has been used to alleviate pain inflammation, and to promote wound healing and tissue regeneration.

The efficacy of the different phototherapies depends on four main factors: irradiance (light intensity), spectral range (wavelength or color), exposed skin surface area, and duration of exposure. Irradiance is a measurement of the light energy incident on the skin (power per surface area per wavelength). Proper application of phototherapy treatments requires assessment of each of these four factors.

SUMMARY

The present disclosure provides an illuminated bassinet including a light source for delivering therapeutic light and anti-bacterial light, where an interlock prevents the anti-bacterial light from being emitted while an infant is located in the bassinet.

The present disclosure provides a surgical illuminator configured to concurrently or alternately emit different wavelengths of light for treating a physiological condition and for affecting perception of the surgical opening.

According to one aspect, there is provided an illuminated bassinet for receiving an infant. The bassinet includes a housing, an electromagnetic radiation source, circuitry, and an interlock. The housing forms a cavity configured to receive the infant. The electromagnetic radiation source is configured to emit electromagnetic radiation into the cavity. The circuitry is configured to control the wavelength of the electromagnetic radiation emitted by the electromagnetic radiation source, such that the electromagnetic radiation source emits: anti-bacterial light comprising electromagnetic radiation having a wavelength that retards or suppresses bacterial growth; and therapeutic light comprising electromagnetic radiation having a wavelength that treats a condition of the infant. The interlock is configured to prevent emission of the anti-bacterial light by the electromagnetic radiation source when the infant is located within the cavity.

Alternatively or additionally, the therapeutic light is chosen to at least one of: treat jaundice or stimulate wound healing.

Alternatively or additionally, the therapeutic light includes a wavelength falling within a range of 460-470 nm or 630-940 nm.

Alternatively or additionally, the anti-bacterial light is chosen to damage bacteria.

Alternatively or additionally, the anti-bacterial light includes a wavelength falling within a range of 400-410 nm or 255-280 nm.

Alternatively or additionally, the interlock comprises at least one of: a combination of a cover configured to engage with a top of the housing and switches positioned such that the switches are toggled when the cover is positioned on the top of the housing; a pressure sensor configured to sense a presence of an infant within the cavity; an RFID sensor configured to sense an RFID chip on the infant when located within the cavity; or an accelerometer configured to sense movement of the infant within the cavity.

Alternatively or additionally, the electromagnetic radiation source comprises a plurality of light sources including a first light source and a second light source. Each of the plurality of light sources is configured to emit light having a wavelength within a particular wavelength range. The wavelength range of the light emitted by the first light source is not identical to the wavelength range of the light emitted by the second light source.

Alternatively or additionally, the electromagnetic radiation source includes a tunable light source and a wavelength of electromagnetic radiation emitted by the tunable light source varies depending on a signal received by the electromagnetic radiation source.

The present disclosure also provides a phototherapy system including the illuminated bassinet and a sensor. The sensor is configured to be worn by an infant or placed in a local environment of the infant and configured to detect in time a wavelength and an intensity of light incident on the sensor. The circuitry is configured to receive an output signal from the sensor based on, for wavelengths of light sensed by the sensor, a time duration and a light intensity of the sensed light. The circuitry is also configured to compare (1) an optical power of the sensed wavelengths of light included in the output signal to (2) a recommended optical power for various wavelengths of light. The circuitry is further configured to control the electromagnetic radiation source to illuminate the cavity with electromagnetic radiation such that the wavelengths of light sensed by the sensor meet or exceed the recommended optical power for the various wavelengths.

The present disclosure further provides a phototherapy system including a bassinet and a sensor. The sensor is configured to be worn by an infant or placed in a local environment of the infant and configured to measure in time a level of jaundice of the infant. The circuitry is configured to: receive an output signal from the sensor indicating the level of jaundice of the infant; and control the electromagnetic radiation source to illuminate the cavity with electromagnetic radiation having a wavelength known to aid in treatment of jaundice at an optical intensity determined based on the level of jaundice of the infant.

The present disclosure additionally provides a surgical illuminator including an electromagnetic radiation source and circuitry. The electromagnetic radiation source configured to emit electromagnetic radiation into a surgical opening. The circuitry is configured to control a wavelength of the electromagnetic radiation emitted by the electromagnetic radiation source, such that the electromagnetic radiation source concurrently or alternately emits: perceiving light comprising electromagnetic radiation having a wavelength chosen to effect perception of the surgical opening; and therapeutic light comprising electromagnetic radiation having a wavelength known to treat a physiological condition.

Alternatively or additionally, emission of the therapeutic light causes a perceived color change of the light emitted by the electromagnetic radiation source. The perceiving light is chosen to offset the perceived color change of the light emitted by the electromagnetic radiation source, such that concurrent emission of the therapeutic light and the perceiving light reduces the perceived color change of the light emitted by the electromagnetic radiation source.

Alternatively or additionally, concurrent emission of the therapeutic light and the perceiving light results in the light emitted by the electromagnetic radiation source appearing white in color.

Alternatively or additionally, the perceiving light comprises light having a wavelength chosen to visually enhance perception of at least one cancerous tissue, noncancerous tissue, blood, veins, nerves, bone, and intervertebral discs, or other tissues that are more readily apparent when illuminated at particular wavelengths.

Alternatively or additionally, the perceiving light and the therapeutic light are: simultaneously emitted; or emitted sequentially such that the perceiving light and the therapeutic light appear to be simultaneously emitted.

Alternatively or additionally, the surgical illuminator further comprises a housing including mounting structures configured to engage a corresponding receiving structure on a surgical instrument.

Alternatively or additionally, the surgical illuminator further comprises a light guide configured to transport electromagnetic radiation from the electromagnetic radiation source to an emission surface of the light guide. The emission surface emits the electromagnetic radiation from the electromagnetic radiation source to illuminate the surgical cavity.

Alternatively or additionally, the light guide is articulable to adjust an area illuminated by the electromagnetic radiation.

Alternatively or additionally, the therapeutic light is chosen to at least one of: stimulate wound healing, retard or suppress bacterial growth, catalyze certain compounds involved in photodynamic therapy, or treat an area for the purposes of photobiomodulation therapy.

Alternatively or additionally, the therapeutic light includes one or more wavelengths falling within a range of 300-1200 nm.

Alternatively or additionally, the circuitry is further configured to for one or more wavelengths of interest, calculate a dose of electromagnetic radiation provided by the electromagnetic radiation source for each of the one or more wavelengths of interest. The circuitry is further configured to, for a given wavelength, receive a desired dose. The circuitry is further configured to, for the given wavelength, control emission by the electromagnetic radiation source of electromagnetic radiation having the given wavelength, such that the desired dose of the given wavelength is provided by the electromagnetic radiation source to the surgical opening.

The present disclosure also provides an overhead surgical lamp for illuminating a surgical area including the illuminator.

The present disclosure further provides an illuminated surgical tool comprising a surgical tool and the illuminator.

While a number of features are described herein with respect to embodiments of the invention; features described with respect to a given embodiment also may be employed in connection with other embodiments. The following description and the annexed drawings set forth certain illustrative embodiments of the invention. These embodiments are indicative, however, of but a few of the various ways in which the principles of the invention may be employed. Other objects, advantages and novel features according to aspects of the invention will become apparent from the following detailed description when considered in conjunction with the drawings.

BRIEF DESCRIPTION OF THE DRAWINGS

The annexed drawings, which are not necessarily to scale, show various aspects of the invention in which similar reference numerals are used to indicate the same or similar parts in the various views.

FIG. 9 is a schematic diagram of a surgical instrument and an embodiment of the surgical illuminator.

FIGS. 10 and 11 are schematic diagrams of a surgical instrument, an embodiment of the surgical illuminator, and a surgical cavity.

DETAILED DESCRIPTION

Figure 1:
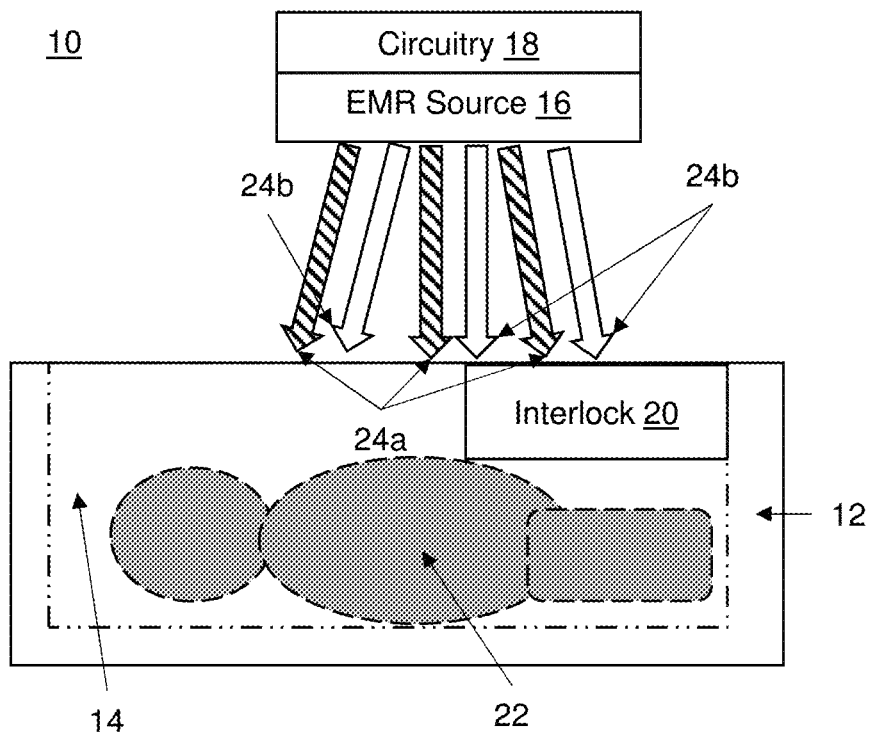
FIG. 1 is a side view of a schematic diagram of an exemplary illuminated bassinet.

The present invention is now described in detail with reference to the drawings. In the drawings, each element with a reference number is similar to other elements with the same reference number independent of any letter designation following the reference number. In the text, a reference number with a specific letter designation following the reference number refers to the specific element with the number and letter designation and a reference number without a specific letter designation refers to all elements with the same reference number independent of any letter designation following the reference number in the drawings.

The present invention provides an illuminated bassinet including an electromagnetic radiation source, an interlock, and circuitry. The circuitry controls the wavelength of electromagnetic radiation emitted by the electromagnetic radiation source. The interlock prevents emission of antibacterial light (having a wavelength that retards or suppresses bacterial growth) when the infant is located within the illuminated bassinet.

Turning to FIG. 1, an exemplary illuminated bassinet 10 for receiving an infant 22 is shown. The illuminated bassinet 10 includes a housing 12, a cavity 14, an electromagnetic radiation source 16, circuitry 18, and an interlock 20. The housing 12 forms a cavity 14 that is configured to receive an infant 22. The electromagnetic radiation source 16 is configured to emit electromagnetic radiation 24 into the cavity 14. The circuitry 18 is configured to control the electromagnetic radiation source 16 to emit anti-bacterial light 24a and therapeutic light 24b. The interlock 20 is configured to prevent emission of the anti-bacterial light 24a by the electromagnetic radiation source 16 when the infant 22 is located within the cavity 14.

With continued reference to FIG. 1, the housing 12 includes a cavity 14 configured to receive an infant 22. The housing 12 may be made of any suitable material. For example, the housing 12 may be made of a plastic that is not adversely affected by the wavelength of the anti-bacterial light 24a and the therapeutic light 24b. Alternatively or additionally, the housing 12 may include a material that attenuates the anti-bacterial light 24a and/or the therapeutic light 24b.

As the cavity 14 may take any suitable shape for receiving an infant. For example, as shown in FIG. 1, the cavity 14 may include walls that prevent the infant 22 from rolling out of the housing 12.

As described above, the electromagnetic radiation source 16 is configured to emit electromagnetic radiation 24 (also referred to as light) into the cavity 14. For example, as shown in FIG. 1, the electromagnetic radiation source 16 may be positioned above the cavity 14. Alternatively, the electromagnetic radiation source 16 may be located within the cavity 14 or in any other suitable position for illuminating the cavity 14. For example, the electromagnetic radiation source 16 may comprise multiple light emitting diodes (LEDs) positioned on side walls of the cavity 14. Alternatively or additionally, the electromagnetic radiation source 16 may comprise a multi-wavelength light source or alternatively a combination of separate sources (e.g., multiple LEDs) emitting electromagnetic radiation having differing wavelengths. For example, the electromagnetic radiation source 16 may comprise separate sources located in different housings that are physically separate from one another.

The electromagnetic radiation source 16 is configured to emit multiple wavelengths of electromagnetic radiation 24 including anti-bacterial light 24a and therapeutic light 24b. The anti-bacterial light 24a comprises electromagnetic radiation having a wavelength that damages bacteria or retards or suppresses bacterial growth. For example, the anti-bacterial light 24a may have a wavelength of 400-410 nm, 255-280 nm, and/or any suitable wavelength shown to retard/suppress bacterial growth or to damage bacteria.

The therapeutic light 24b comprises electromagnetic radiation having a wavelength that treats a condition of the infant 22. For example, the therapeutic light may be chosen to at least one of: treat jaundice or stimulate wound healing. As an example, the therapeutic light 24b may include a wavelength falling within a range of 460-470 nm or 630-940 nm.

The circuitry 18 is configured to control the wavelength of the electromagnetic radiation 24 emitted by the electromagnetic radiation source 16. For example, the circuitry 18 provides an output signal to the electromagnetic radiation source 16 identifying the parameters to be used to generate a particular wavelength of electromagnetic radiation 24.

As described above, the interlock 20 is configured to prevent emission of the anti-bacterial light 24a by the electromagnetic radiation source 16 when the infant 22 is located within the cavity 14. For example, the interlock 20 may comprise a combination of a cover configured to engage with a top of the housing and switches positioned such that the switches are toggled when the cover is positioned on the top of the housing. In this way, the interlock 20 may control the electromagnetic radiation source 16 such that anti-bacterial light 24a is only emitted when the lid is located on the top of the housing 12 (i.e., when the infant is not located within the cavity 14). Alternatively or additionally, the interlock may include a sensor configured to directly sense a presence of an infant 22 within the cavity 14. For example, the interlock 20 may comprise a pressure sensor configured to detect a weight of the infant 22 within the cavity 14, an RFID sensor configured to sense an RFID chip on the infant 22 when located within the cavity (e.g., an RFID bracelet frequently placed on newborn infants in the hospital), and/or an accelerometer configured to sense movement of the infant within the cavity 14. As will be understood by one of ordinary skill in the art, the interlock 20 is not limited to these sensors listed above, but may include any suitable sensor (e.g., an infrared (IR) occupancy sensor, a camera or an opto switch, etc.).

In addition to the anti-bacterial light 24a, the interlock 20 may also prevent emission of wavelengths of electromagnetic radiation 24 other than the anti-bacterial light 24a. In an alternative embodiment, the electromagnetic radiation source 16 may only emit anti-bacterial light 24a (i.e., not emit therapeutic light 24b) and the interlock 20 may be used to prevent emission of electromagnetic radiation 24 while an infant 22 is located within the cavity 14.

As will be understood by one of ordinary skill in the art, the interlock 20 may interact with the circuitry 18 to prevent emission of the anti-bacterial light 24a by the electromagnetic radiation source 16 when the infant 22 is located within the cavity 14. For example, the circuitry 18 may receive a signal from the interlock 20. The circuitry 18 may then determine whether an infant is located within the cavity 14 based on the received signal from the interlock 20. For example, when receiving a signal from a pressure sensor or accelerometer, the circuitry 18 may determine that an infant 22 is located within the cavity 14 (and consequently prevent the electromagnetic radiation source 16 from outputting anti-bacterial light 24a) if the received signal is greater than a threshold.

Figure 2:
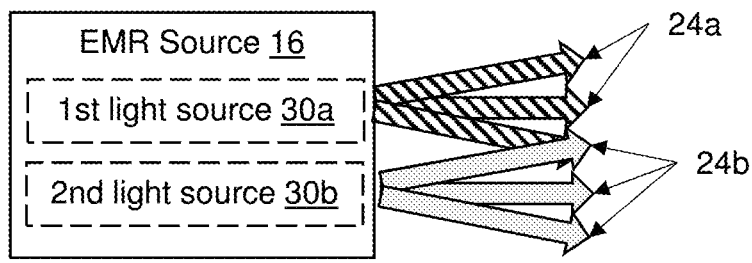
FIG. 2 is a schematic diagram of an electromagnetic radiation source including a plurality of light sources.

The electromagnetic radiation source 16 may comprise any suitable source of electromagnetic radiation capable of outputting the wavelength(s) of the anti-bacterial light 24a and the wavelength(s) of the therapeutic light 24b. For example, as shown in FIG. 2, the electromagnetic radiation source 16 may comprise a plurality of light sources 30 including a first light source 30a and a second light source 30b. Each of the plurality of light sources 30 may be configured to emit light having a wavelength within a particular wavelength range. The wavelength range of the light emitted by the first light source 30a may be different from (i.e., not identical to) the wavelength range of the light emitted by the second light source 30b.

For example, the plurality of light sources 30 may comprise light emitting diodes (LEDs), with the first light source 30a comprising a first LED and the second light source 30b comprising a second separate LED. As shown in FIG. 2, the first LED 30a may emit electromagnetic radiation 24 having a wavelength range of the anti-bacterial light 24a. In this way, when the circuitry 18 controls the electromagnetic radiation source 16 to emit anti-bacterial light 24a, the first LED 30a may be activated. Similarly, the second LED 30b may emit electromagnetic radiation 24 having a wavelength range of the therapeutic light 24b. In this way, when the circuitry 18 controls the electromagnetic radiation source 16 to emit therapeutic light 24b, the second LED 30b may be activated.

In another embodiment, the plurality of light sources 30 may comprise a first, second, third, and fourth light source 30, with each of the first, second, third, and fourth light sources 30 emitting electromagnetic radiation having a different wavelength range. In this embodiment, a combination of the wavelengths of electromagnetic radiation emitted by the first and second light sources may together include the wavelengths of the anti-bacterial light 24a. Consequently, the circuitry 18 may cause the first and second light sources to emit light simultaneously or sequentially when controlling the electromagnetic radiation source 16 to emit anti-bacterial light 24a. Similarly, in this embodiment, a combination of the wavelengths of electromagnetic radiation emitted by the third and fourth light sources may together include the wavelengths of the therapeutic light 24b. Consequently, the circuitry 18 may cause the third and fourth light sources to emit light simultaneously or sequentially when controlling the electromagnetic radiation source 16 to emit therapeutic light 24b.

As will be understood by one of ordinary skill in the art, while the above describes a first light source, a second light source, a third light source, and a fourth light source, the first, second, third, and fourth light sources are not each limited to a singular light source. That is, each of the first, second, third, and fourth light sources may include multiple LEDs. That is, the first light source may comprise a plurality of LEDs, the second light source may comprise a plurality of LEDs, the third light source may comprise a plurality of LEDs, and the fourth light source may comprise a plurality of LEDs.

Figure 3:
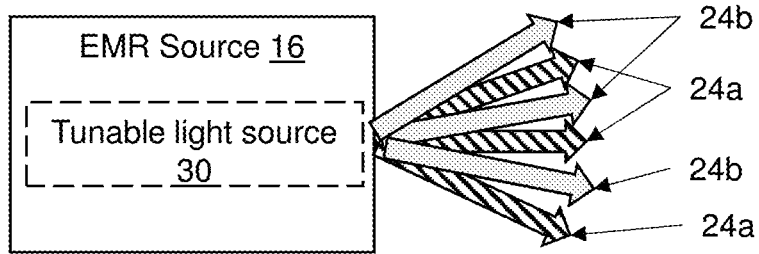
FIG. 3 is a schematic diagram of an electromagnetic radiation source including a tunable light source.

In an alternative embodiment shown in FIG. 3, the electromagnetic radiation source 16 may include a tunable light source 30, where a wavelength of electromagnetic radiation 24 emitted by the tunable light source 30 varies depending on a signal received by the electromagnetic radiation source 16. That is, the electromagnetic radiation source 16 may include a single light source 30 that is tunable to vary the wavelength of the electromagnetic radiation 24 output by the tunable light source 30. For example, the tunable light source 30 may first output anti-bacterial light 24a using a single tunable LED 30 and the same single tunable LED 30 may then be used to output therapeutic light 24b.

As will be understood by one of ordinary skill in the art, the light source(s) 30 are not limited to LEDs, but may comprise any suitable source of electromagnetic radiation 24.

Figure 4:
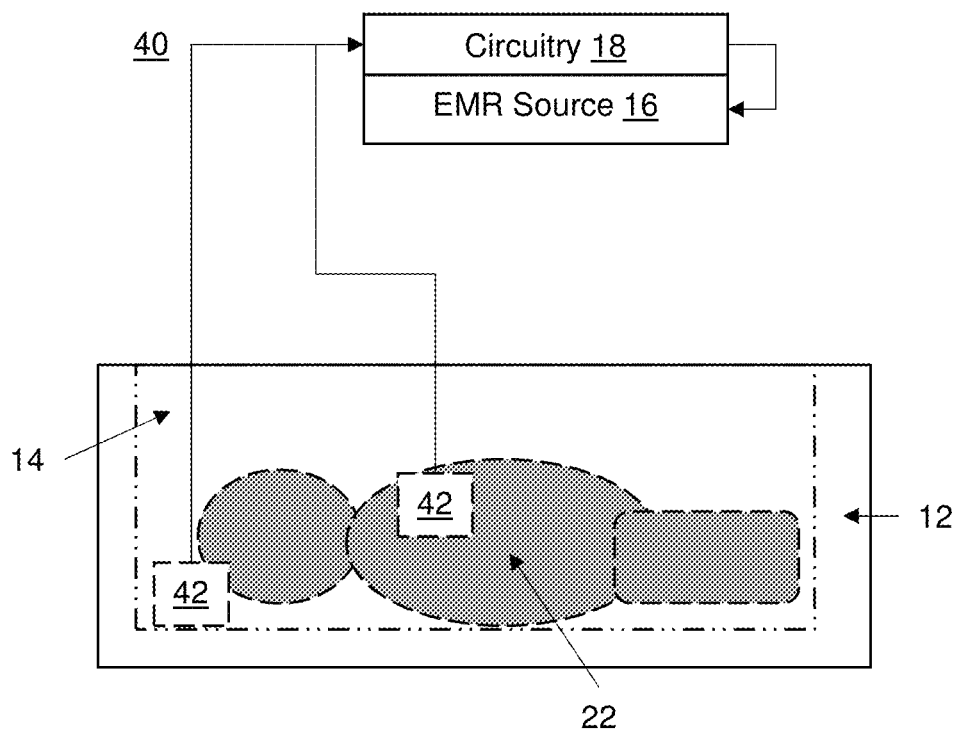
FIG. 4 is a side view of a schematic diagram of a phototherapy system including a sensor and the illuminated bassinet of FIG. 1.

Turning to FIG. 4, a phototherapy system 40 including the illuminated bassinet 10 and a sensor 42 is shown. The sensor 42 is configured to be worn by an infant 22 or to be placed in a local environment of the infant 22 (e.g., in the cavity 14). The sensor 42 is configured to detect in time a wavelength and an intensity of light incident on the sensor 42. For example, the sensor 42 may comprise a photodiode or any other suitable light sensor capable of measuring the optical power and wavelength of light incident on the sensor.

With continued reference to FIG. 4, the circuitry 18 may be configured to receive an output signal from the sensor 42 based on, for the wavelengths of light sensed by the sensor 42, a time duration and a light intensity of the sensed light. That is, the circuitry 18 may receive from the sensor 42 a signal indicating (1) a particular wavelength of light and (2) a light intensity and (3) time duration of light sensed by the sensor 42 having the particular wavelength. The sensor 42 may report to the circuitry 18 data on all wavelengths sensed by the sensor 42 or, alternatively, only report data on a subset of the wavelengths sensed by the sensor 42 (e.g., particular wavelength range(s) of interest).

The circuitry 16 may compare (1) an optical power of the sensed wavelengths of light included in the output signal to (2) a recommended optical power for various wavelengths of light. The circuitry 16 may then control the electromagnetic radiation source 16 to illuminate the cavity 14 with electromagnetic radiation 24, such that the wavelengths of light sensed by the sensor 42 meet or exceed the recommended optical power for the various wavelengths. For example, if the sensor 42 indicates that the optical power of electromagnetic radiation having a wavelength in the range 500-530 nm is below the recommend optical power for the wavelength range 500-530 nm, the circuitry 16 may increase the optical power output by the electromagnetic radiation source 16 until the optical power sensed by the sensor 42 for electromagnetic radiation having a wavelength of 500-530 nm matches the recommend optical power.

Figure 5:
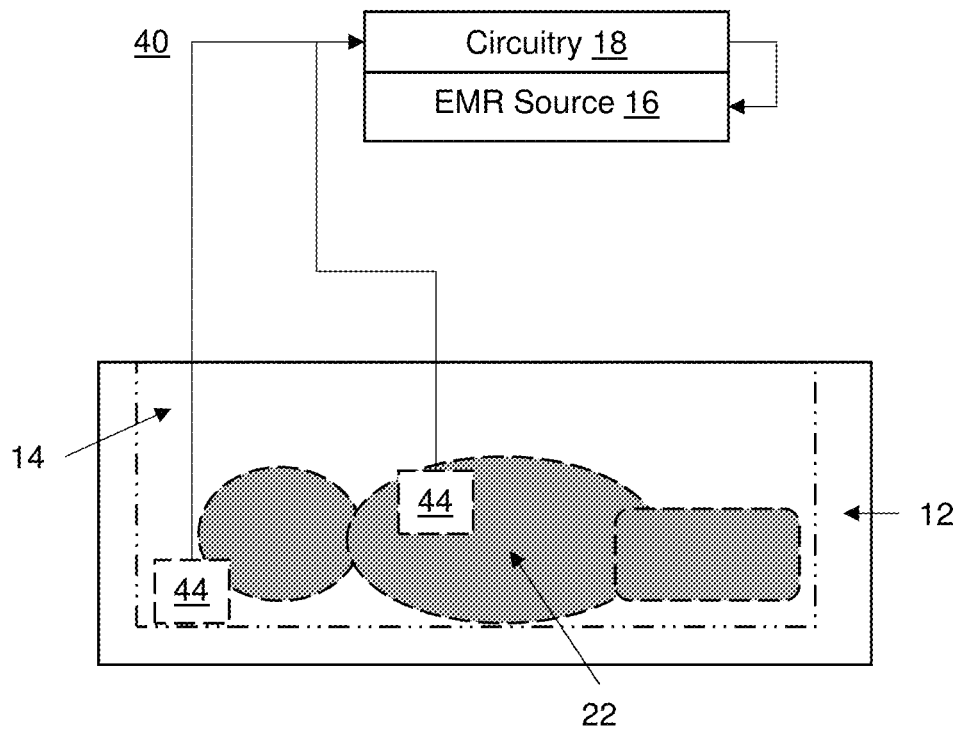
FIG. 5 is a side view of a schematic diagram of a phototherapy system including a physiological sensor and the illuminated bassinet of FIG. 1.

Turning to FIG. 5, the phototherapy system 40 may include the illuminated bassinet 10 and a physiological sensor 44. The physiological sensor 44 may be configured to be worn by an infant 22 or placed in a local environment of the infant and configured to measure in time a level of jaundice of the infant 22. The physiological sensor 44 may comprise any sensor suitable for measuring a jaundice level of the infant 22. For example, the physiological sensor 44 may comprise a photodiode and corresponding light source configured to measure a color of the infant's skin.

With continued reference to FIG. 5, the circuitry 18 may be configured to receive an output signal from the physiological sensor 44 indicating the level of jaundice of the infant 22. The circuitry 18 may then control the electromagnetic radiation source 16 to illuminate the cavity 14 with electromagnetic radiation 24 having a wavelength known to aid in treatment of jaundice at an optical intensity determined based on the level of jaundice of the infant 22. For example, if a level of the infant's jaundice is within a given range, the circuitry 18 may control the electromagnetic radiation source 16 to generate electromagnetic radiation 24 having a predetermined wavelength range and a predetermined intensity.

As will be understood by one of ordinary skill in the art, the sensor 42 and physiological sensor 44 may be used simultaneously. That is, the circuitry 18 may receive output signals from both the sensor 42 and the physiological sensor 44 and the circuitry 18 may control the electromagnetic radiation source 16 according to the output signals from both the sensor 42 and the physiological sensor 44. The sensor 42 and physiological sensor 44 may additionally comprise a single device. For example, the sensor 42 and the physiological sensor 44 may be located within a same housing.

Figure 6:
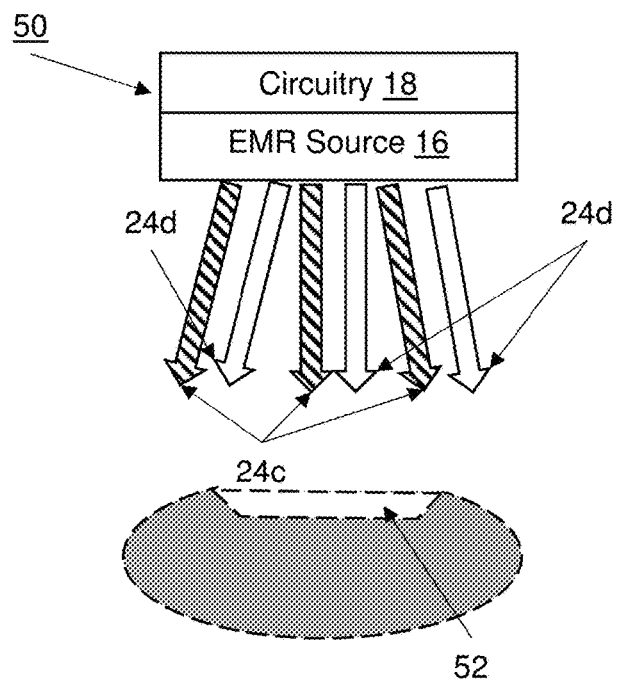
FIG. 6 is a side view of a schematic diagram of a surgical illuminator.

Turning to FIG. 6, a surgical illuminator 50 is shown. The surgical illuminator 50 includes an electromagnetic radiation source 16 and circuitry 18. The electromagnetic radiation source 16 is configured to emit electromagnetic radiation 24 into a surgical opening 52. For example, the surgical illuminator 50 may include a same or similar electromagnetic radiation source 16 as described above in reference to the illuminated bassinet 10. The circuitry 18 is configured to control a wavelength of the electromagnetic radiation 24 emitted by the electromagnetic radiation source 16, such that the electromagnetic radiation source 16 concurrently or alternately emits perceiving light 24c and therapeutic light

24d. The perceiving light 24d comprises electromagnetic radiation 24 having a wavelength chosen to effect perception of the surgical opening 52. The therapeutic light 24d comprises electromagnetic radiation 24 having a wavelength known to treat a physiological condition.

The therapeutic light 24d may be chosen to at least one of: stimulate wound healing, retard or suppress bacterial growth, catalyze certain compounds involved in photodynamic therapy, or treat an area for the purposes of photobiomodulation therapy. For example, the therapeutic light 24d may include a wavelength falling within a range of 300-1200 nm. As an example, the therapeutic light 24d may include wavelengths used for PBM (600-1100 nm) and/or for photodynamic therapy (PDT) (300-1200 nm). The wavelength and intensity of the therapeutic light 24d are not limited to these applications, but may be chosen to treat any physiological condition.

Emission of the therapeutic light 24d may cause a perceived color change of the light emitted by the electromagnetic radiation source 16. For example, in FIG. 7 therapeutic light 24d in the red spectrum is emitted. In this example, the electromagnetic radiation 24 emitted by the electromagnetic radiation source 16 is a combination of the therapeutic light 24d and the perceiving light 24c. Because in this example the perceiving light 24c is white (i.e., is broad spectrum), the resulting total electromagnetic radiation emitted by the electromagnetic radiation source 16 will appear to be red shifted due to the inclusion of the therapeutic light 24d.

Figure 8:
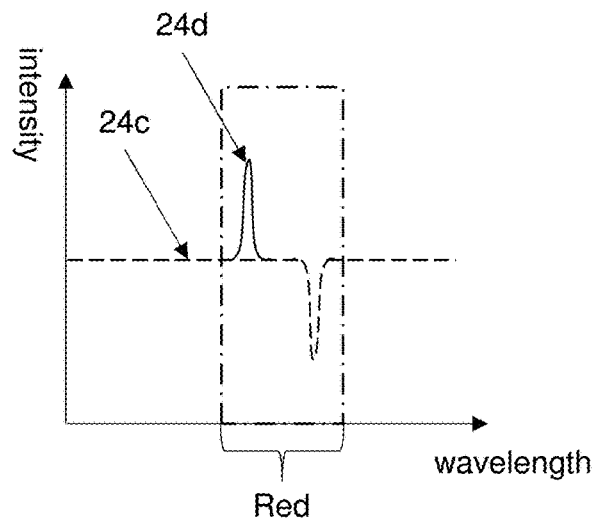
FIG. 8 is an exemplary plot of perceiving light and therapeutic light including compensation that has been emitted by the surgical illuminator of FIG. 6.

As shown in FIG. 8, the perceiving light 24c may be chosen to offset the perceived color change of the light emitted by the electromagnetic radiation source, such that concurrent emission of the therapeutic light 24d and the perceiving light 24c reduces the perceived color change of the light emitted by the electromagnetic radiation source 16. As an example, concurrent emission of the therapeutic light 24d and the perceiving light 24c may results in the light emitted by the electromagnetic radiation source 16 appearing white in color.

For example, the perceiving light 24d may be modified to reduce the emission of a wavelength of electromagnetic radiation that is perceived as the same color, but that is different from the wavelength of the therapeutic light 24c. As an example, in FIG. 8, the therapeutic light 24c comprises a wavelength of light perceived as red. To avoid the light emitted by the electromagnetic radiation source 16 being perceived as red shifted, the perceiving light 24c is altered to reduce the intensity of a higher wavelength red light than the wavelength of the therapeutic light 24d.

As will be understood by one of ordinary skill in the art, the therapeutic light 24d and perceiving light 24c are not limited to having the profiles shown in the figures. For example, the figures do not show how the relationship between actual intensity of light and perceived intensity of light differ for different wavelengths of light. Consequently, the compensation by the perceiving light 24c for the therapeutic light 24d may require that the alteration of the perceiving light 24c have a different magnitude than the intensity of the alteration of the therapeutic light 24c.

Further, as will be understood by one of ordinary skill in the art, the compensation for the therapeutic light 24d may only be required for those wavelengths of the therapeutic light 24d that are perceived by the human visual system. For example, invisible infrared or UV light may not be compensated for by the perceiving light 24c.

The perceiving light 24c is not limited to compensation for the visual effect caused by the therapeutic light 24d. For example, the perceiving light 24d may include light having a wavelength chosen to visually enhance perception of at least one cancerous tissue, noncancerous tissue, blood, veins, nerves, bone, and intervertebral discs, or other tissues that are more readily apparent when illuminated at particular wavelengths. As an example, when performing surgery, there may be blood covering many of the tissues. To increase the visibility of the other tissues in the surgical cavity, the perceiving light may include a broad spectrum of wavelengths with the red component removed or the intensity of the red component made to be lower than the other wavelengths. That is, the perceiving light may have a larger component of green and blue light than red light. In this way, the perceiving light may be used to increase the visibility of tissues of interest by reducing or removing the color component of light found in other tissues surrounding the tissues of interest.

Figure 7:
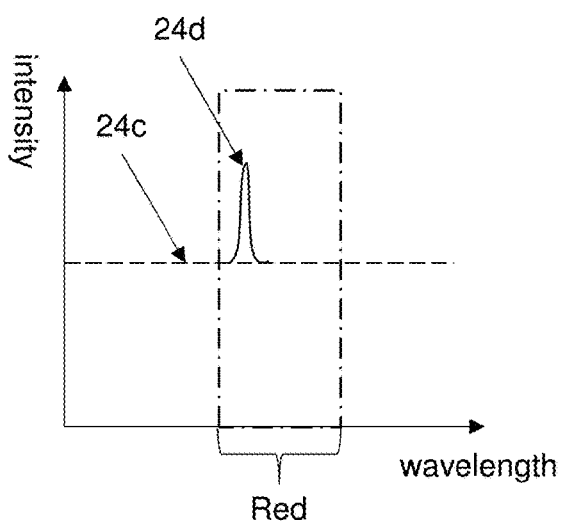
FIG. 7 is an exemplary plot of perceiving light and therapeutic light without compensation that has been emitted by the surgical illuminator of FIG. 6.

The perceiving light 24c and the therapeutic light 24d may be simultaneously emitted as shown in FIGS. 7 and 8. Alternatively, the perceiving light 24c and the therapeutic light 24d may be emitted sequentially, such that the perceiving light and the therapeutic light appear to be simultaneously emitted. For example, emission of the perceiving light 24c and the therapeutic light 24d may be alternated at a frequency that is too fast to be perceived by humans, causing the perceiving light 24c and the therapeutic light 24d to appear to be emitted simultaneously.

Turning to FIG. 9, the surgical illuminator may include a housing 60 having mounting structures 62 configured to engage corresponding receiving structures 72 on a surgical instrument 70.

Turning to FIG. 10, the surgical illuminator 50 may additionally include a light guide 80 configured to transport electromagnetic radiation 24 from the electromagnetic radiation source 16 to an emission surface 82 of the light guide 80. The emission surface 82 emits the electromagnetic radiation 24 from the electromagnetic radiation source 16 to illuminate the surgical cavity 52. As shown in FIG. 11, the light guide 80 may be articulable to adjust an area illuminated 86 by the electromagnetic radiation 24.

As shown in the FIGS. 6 and 9-11, the surgical illuminator 50 may take different forms. For example, as shown in FIG. 6, the illuminator 50 may be included in an overhead surgical lamp for illuminating a surgical area. Alternatively, the illuminator 50 may be included in a surgical tool as shown in FIGS. 9-11.

The circuitry 18 of the illuminator 50 may be further configured to: for one or more wavelengths of interest, calculate a dose of electromagnetic radiation provided by the electromagnetic radiation source for each of the one or more wavelengths of interest. The circuitry 18 may also receive, for a given wavelength, a desired dose. For the given wavelength, the circuitry 18 may control emission by the electromagnetic radiation source of electromagnetic radiation having the given wavelength, such that the desired dose of the given wavelength is provided by the electromagnetic radiation source 16 to the surgical opening 52. For example, the circuitry 18 may receive as an input an estimated duration of a surgical procedure and the circuitry 18 may calculate the intensity profile vs time for the one or more wavelengths of interest based on the estimated duration of the surgical procedure.

As will be understood by one of ordinary skill in the art, the circuitry 18 may have various implementations. For example, the circuitry 18 may include any suitable device, such as a processor (e.g., CPU), programmable circuit, integrated circuit, memory and I/O circuits, an application specific integrated circuit, microcontroller, complex programmable logic device, other programmable circuits, or the like. The circuitry 18 may also include a non-transitory computer readable medium, such as random access memory (RAM), a read-only memory (ROM), an erasable programmable read-only memory (EPROM or Flash memory), or any other suitable medium. Instructions for performing the operations described above may be stored in a non-transitory computer readable medium and executed by the circuitry 18. The circuitry 18 may be communicatively coupled to a computer readable medium and a network interface through a system bus, mother board, or using any other suitable structure known in the art. The circuitry 18 may be located within a same or different housing than the electromagnetic radiation source 16.

It should be appreciated that many of the elements discussed in this specification may be implemented in a hardware circuit(s), a processor executing software code or instructions which are encoded within computer readable media accessible to the processor, or a combination of a hardware circuit(s) and a processor or control block of an integrated circuit executing machine readable code encoded within a computer readable media. As such, the term circuit, module, server, application, or other equivalent description of an element as used throughout this specification is, unless otherwise indicated, intended to encompass a hardware circuit (whether discrete elements or an integrated circuit block), a processor or control block executing code encoded in a computer readable media, or a combination of a hardware circuit(s) and a processor and/or control block executing such code.

All ranges and ratio limits disclosed in the specification and claims may be combined in any manner. Unless specifically stated otherwise, references to "a," "an," and/or "the" may include one or more than one, and that reference to an item in the singular may also include the item in the plural.

Although the invention has been shown and described with respect to a certain embodiment or embodiments, equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

The invention claimed is:

1. An illuminated bassinet for receiving an infant, the bassinet comprising:
   a housing forming a cavity configured to receive the infant;
   an electromagnetic radiation source configured to emit electromagnetic radiation into the cavity;
   circuitry configured to control the wavelength of the electromagnetic radiation emitted by the electromagnetic radiation source, such that the electromagnetic radiation source emits:
   anti-bacterial light comprising electromagnetic radiation having a wavelength that retards or suppresses bacterial growth; and
   therapeutic light comprising electromagnetic radiation having a wavelength that treats a condition of the infant; and
   an interlock configured to prevent emission of the anti-bacterial light by the electromagnetic radiation source when the infant is located within the cavity.

2. The bassinet of claim 1, wherein the therapeutic light is chosen to at least one of: treat jaundice or stimulate wound healing.

3. The bassinet of claim 2, wherein the therapeutic light includes a wavelength falling within a range of 460-470 nm or 720-740 nm.

4. The bassinet of claim 1, wherein the anti-bacterial light includes a wavelength falling within a range of 400-410 nm or 255-280 nm.

5. The bassinet of claim 1, wherein the interlock comprises at least one of:
   a combination of a cover configured to engage with a top of the housing and switches positioned such that the switches are toggled when the cover is positioned on the top of the housing;
   a pressure sensor configured to sense a presence of an infant within the cavity;
   an RFID sensor configured to sense an RFID chip on the infant when located within the cavity; or
   an accelerometer configured to sense movement of the infant within the cavity.

6. The bassinet of claim 1, wherein:
   the electromagnetic radiation source comprises a plurality of light sources including a first light source and a second light source;
   each of the plurality of light sources is configured to emit light having a wavelength within a particular wavelength range;
   the wavelength range of the light emitted by the first light source is not identical to the wavelength range of the light emitted by the second light source.

7. The bassinet of claim 1, wherein:
   the electromagnetic radiation source includes a tunable light source; and
   a wavelength of electromagnetic radiation emitted by the tunable light source varies depending on a signal received by the electromagnetic radiation source.

8. A phototherapy system comprising:
   a sensor configured to be worn by an infant or placed in a local environment of the infant and configured to detect in time a wavelength and an intensity of light incident on the sensor;
   the bassinet of claim 1, wherein the circuitry is configured to:
   receive an output signal from the sensor based on, for wavelengths of light sensed by the sensor, a time duration and a light intensity of the sensed light;
   compare (1) an optical power of the sensed wavelengths of light included in the output signal to (2) a recommended optical power for various wavelengths of light; and
   control the electromagnetic radiation source to illuminate the cavity with electromagnetic radiation such that the wavelengths of light sensed by the sensor meet or exceed the recommended optical power for the various wavelengths.

9. A phototherapy system comprising:
a sensor configured to be worn by an infant or placed in a local environment of the infant and configured to measure in time a level of jaundice of the infant;
the bassinet of claim 1, wherein the circuitry is configured to:
  receive an output signal from the sensor indicating the level of jaundice of the infant; and
  control the electromagnetic radiation source to illuminate the cavity with electromagnetic radiation having a wavelength known to aid in treatment of jaundice at an optical intensity determined based on the level of jaundice of the infant.

* * * * *